United States Patent
Lee et al.

(10) Patent No.: US 9,478,756 B2
(45) Date of Patent: Oct. 25, 2016

(54) ORGANOMETALLIC COMPOUND, AND ORGANIC LIGHT-EMITTING DIODE USING SAME

(75) Inventors: Jaemin Lee, Daejeon (KR); Chan Hyuk Park, Gyeonggi-do (KR); Sung Cheol Yoon, Gyeonggi-do (KR); Jongsun Lim, Daejeon (KR); Young Hun Kang, Busan (KR); Chang Jin Lee, Daejeon (KR)

(73) Assignee: KOREA RESEARCH INSTITUTE OF CHEMICAL TECHNOLOGY, Daejeon-si (KR)

(*) Notice: Subject to any disclaimer, the term of this patent is extended or adjusted under 35 U.S.C. 154(b) by 566 days.

(21) Appl. No.: 14/002,598

(22) PCT Filed: Apr. 6, 2012

(86) PCT No.: PCT/KR2012/002624
§ 371 (c)(1),
(2), (4) Date: Aug. 30, 2013

(87) PCT Pub. No.: WO2012/138172
PCT Pub. Date: Oct. 11, 2012

(65) Prior Publication Data
US 2013/0334521 A1 Dec. 19, 2013

(30) Foreign Application Priority Data

Apr. 6, 2011 (KR) .................. 10-2011-0031767

(51) Int. Cl.
*H01L 51/00* (2006.01)
*C07D 213/24* (2006.01)
*C09K 11/06* (2006.01)
(Continued)

(52) U.S. Cl.
CPC ......... *H01L 51/0085* (2013.01); *C07D 213/24* (2013.01); *C07F 15/0033* (2013.01);
(Continued)

(58) Field of Classification Search
None
See application file for complete search history.

(56) References Cited

U.S. PATENT DOCUMENTS 6,303,238 B1   10/2001   Thompson et al.

FOREIGN PATENT DOCUMENTS

| JP | 2002-008860 A | 1/2002 |
| JP | 2007-016196 A | 1/2007 |

(Continued)

OTHER PUBLICATIONS

Zhou et al. (Adv. Funct. Mater. 2008, 18, p. 499).*

*Primary Examiner* — J. L. Yang
(74) *Attorney, Agent, or Firm* — Ladas & Parry LLP

(57) ABSTRACT

The present invention relates to a novel organometallic compound, and more particularly, to a luminescent organometallic compound in which intermolecular interaction is inhibited by means of introducing a germanium substituent, thereby improving light-emitting characteristics. The present invention also relates to an organic electronic device, specifically, to an organic light-emitting diode using the compound. According to the present invention, a germanium substituent is introduced to the parent organometallic iridium compound, thus inhibiting an intermolecular interaction in the solid state and enabling the compound of the present invention to be effectively used in solution processing. When the compound of the present invention is used as part of a light-emitting layer of an organic light-emitting diode, the light-emitting efficiency of the light-emitting diode may be significantly improved. Therefore, the compound of the present invention may be effectively used as a material for an organic light-emitting diode.

18 Claims, 8 Drawing Sheets

(51) Int. Cl.
  *H05B 33/14* (2006.01)
  *C07F 15/00* (2006.01)
  *H01L 51/50* (2006.01)

(52) U.S. Cl.
  CPC ............... *C09K11/06* (2013.01); *H05B 33/14* (2013.01); *C09K 2211/1014* (2013.01); *C09K 2211/1029* (2013.01); *C09K 2211/185* (2013.01); *H01L 51/5016* (2013.01)

(56) References Cited

FOREIGN PATENT DOCUMENTS

| JP | 3-992929 B2 | 10/2007 |
| KR | 1020050080288 A | 8/2005 |
| WO | 2008/153088 A1 | 12/2008 |

* cited by examiner

ORGANOMETALLIC COMPOUND, AND ORGANIC LIGHT-EMITTING DIODE USING SAME

CROSS-REFERENCE TO RELATED APPLICATIONS

This patent application is a U.S. national phase under 35 U.S.C 371 of PCT/KR2012/002624 filed on Apr. 6, 2012, which claims the benefit of priority from Korean Patent Applications No. 10-2011-0031767 filed on Apr. 6, 2011 in the Korean Intellectual Property Office, the disclosure of which is incorporated herein by reference in its entirety.

BACKGROUND

1. Field of the Invention

The present invention relates to a novel organometallic compound, and more particularly, to a light-emitting organometallic compound with improved light-emitting property, in which a germanium substituent is introduced, inhibiting intermolecular interaction, an organic electronic device, or an organic light-emitting diode using the organometallic compound.

2. Description of the Related Art

Organic light-emitting diode (OLED) is a kind of organic electronic device, which basically includes an organic thin film including an organic light-emitting layer is sandwiched between two electrodes, in which at least one of the electrodes is transparent, to utilize the light in visible-light range emitted from the organic light-emitting layer upon application of a proper voltage, e.g., direct current of 5~10V, for example.

The organic light-emitting diode is very thin, with actual thickness including the electrodes ranging only several micrometers or less, and is a self-light emitting diode that emits light directly from the diode itself, and accordingly has various advantages because it has a fast responsivity, provides a display device with a broad viewing angle, requires simple manufacturing process, achieves flexibility using organic thin film, can be fabricated by not only vacuum process, but also printing process in a solution state as need arises. Thus, the organic light-emitting diode is gaining a huge attention as a next-generation display and illumination, for which active researches are under way.

Generally, the organic light-emitting layer includes at least one of organic and organometallic compound or organic/inorganic hybrid materials, and is divided into two types according to light-emitting mechanism: one is a fluorescence type based on quenching of singlet exciton, and the other is a phosphorescence type using quenching of triplet exciton.

The phosphorescence type using the triplet exciton, in particular, has been applied to organic light-emitting diodes relatively recently compared to the fluorescence one (refer to U.S. Pat. No. 6,303,238.). Since the latter type creates a higher efficiency than the fluorescence one, research on related technologies has been conducted very briskly.

For the organic light-emitting diode of the phosphorescence type, the most important key element is phosphorescent light-emitting substance such as widely known organometallic compounds. Among these, the organometallic compounds based mainly on iridium prevail.

The iridium organometallic compounds have an advantage in that the optical and electrical properties of the final iridium organometallic compounds are adjustable by regulating the chemical structure of a ligand coordinate bond to an iridium atom, to enable synthesis of organometallic compounds that suit various requirements.

Specifically, the iridium organometallic compounds having phenylpyridine as a basic structure of ligand, e.g. tris (2-phenylpyridine)iridium (III) (hereinafter referred to as 'Ir(ppy)$_3$'), are the most widely known (refer to JP 3992929.).

However, the conventionally known iridium organometallic compound such as Ir(ppy)$_3$ has limited efficiency due to triplet annihilation caused by intermolecular interaction when used as a light-emitting layer of an organic light-emitting diode. Also, the solubility in a solvent may not be sufficient when used in the solution process, instead of vacuum deposition.

Therefore, there are growing requests to develop light-emitting organometallic compounds that are applicable to the solution process and have an improved light-emitting property.

Accordingly, the inventors of the present invention have completed the present invention, in the course of researching solution to the foregoing shortcomings, after synthesizing a novel organometallic compound with improved emission efficiency due to inhibited intermolecular interaction by the introduction of a germanium substituent into an iridium ligand and confirming that the light-emitting property of the compound is improved compared to that of conventional organometallic compounds, and thus is applicable to an organic light-emitting diode.

SUMMARY OF THE INVENTION

The objective of the present invention is to provide a novel organometallic compound for use in an organic light-emitting diode.

Another objective of the present invention is to provide an organic light-emitting diode including the novel organometallic compound therein.

In order to achieve the aforementioned objectives, the present invention provides a novel organometallic compound represented by Formula 1 below.

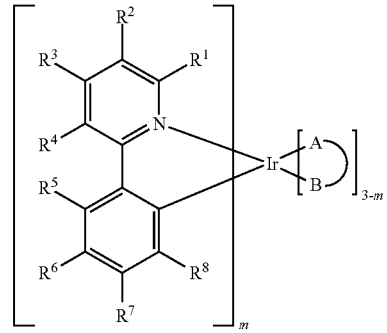

[Formula 1]

(In Formula 1 above, $R^1$~$R^8$,

and m are as defined herein.)

Further, the present invention provides an organic light-emitting diode containing the novel organometallic compound.

Furthermore, the present invention provides a method for forming a thin film for an organic light-emitting diode, which includes the following steps of:

preparing a solution by dissolving a novel organometallic compound in an organic solvent (step 1); and forming a thin film on a substrate by dropping the solution prepared at step 1 onto the substrate and rotating and drying the substrate (step 2).

According to the present invention, since a germanium substituent is incorporated into a parent organometallic iridium compound, intermolecular interaction is controlled in the solid state and the organometallic compound of the present invention can be effectively used in the solution processing. Further, when the compound of the present invention is used as part of a light-emitting layer of an organic light-emitting diode, the emission efficiency of the light-emitting diode is improved significantly. Therefore, the organometallic compound of the present invention may be effectively used as a material for an organic light-emitting diode.

DESCRIPTION OF THE PREFERRED EMBODIMENT

Figure 1:
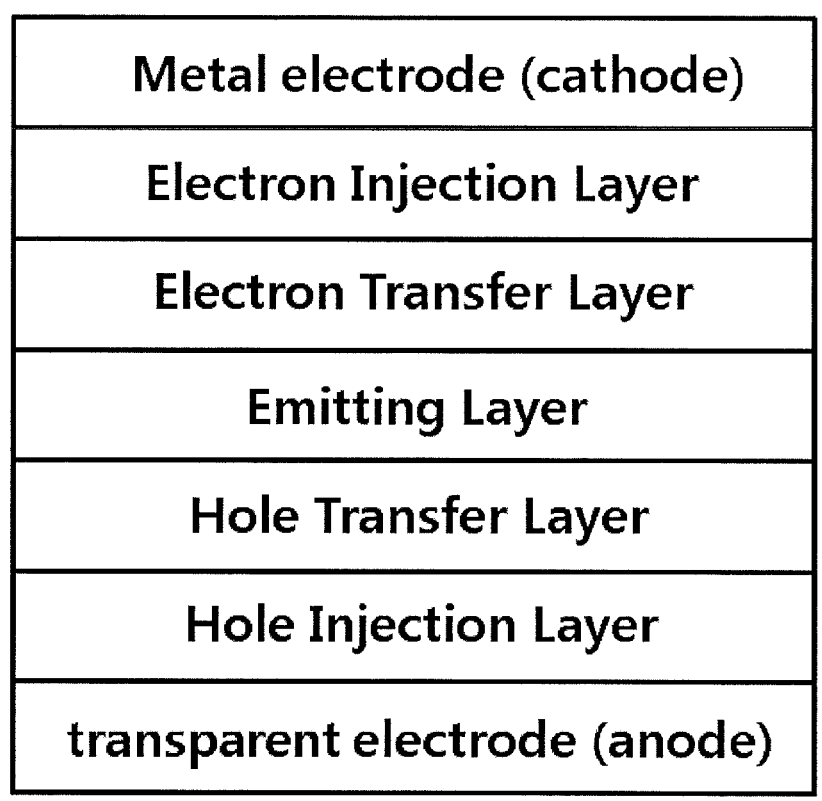
FIGS. 1 to 3 are schematic sectional views of organic light-emitting diodes according to the present invention.

Hereinafter, the present invention will be described in detail.

The organometallic compound according to the present invention is represented by Formula 1 below:

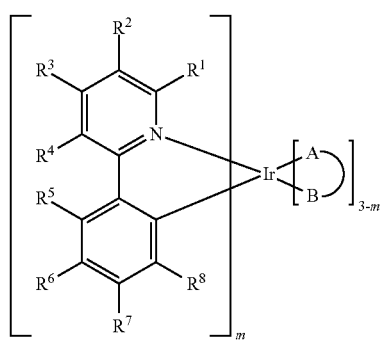

[Formula 1]

(In Formula 1 above, at least one among $R^1$ to $R^4$ is a substituent represented by Formula 2 below;

if there is no substituent of Formula 2 among $R^1$ to $R^4$, $R^1$ to $R^4$ are independent ones from each other selected from the group consisting of hydrogen, deuterium, halogen, cyano, $C_1$-$C_{18}$ straight or branched alkyl, $C_1$-$C_{18}$ straight or branched alkoxy, $C_6$-$C_{18}$ aryl, $C_3$-$C_{18}$ cycloalkyl, $C_4$-$C_{18}$ heteroaryl, and 5 to 6-membered heterocycloalkyl, where, the alkyl or alkoxy is non-substitutable or substituted with halogen; the aryl, cycloalkyl, heteroaryl, or heterocycloalkyl is non-substitutable or substituted with halogen or $C_1$-$C_{18}$ straight or branched alkyl; and the heteroaryl or heterocycloalkyl contains at least one atom selected from among N, O, and S in the ring;

$R^5$ to $R^8$ are independent ones from each other selected from the group consisting of hydrogen, deuterium, halogen, cyano, $C_1$-$C_{18}$ straight or branched alkyl, $C_1$-$C_{18}$ straight or branched alkoxy, $C_6$-$C_{18}$ aryl, $C_3$-$C_{18}$ cycloalkyl, $C_4$-$C_{18}$ heteroaryl, and 5 to 6-membered heterocycloalkyl, where, the alkyl or alkoxy is non-substitutable or substituted with halogen; the aryl, cycloalkyl, heteroaryl, or heterocycloalkyl is non-substitutable or substituted with halogen or $C_1$-$C_{18}$ straight or branched alkyl; and the heteroaryl or heterocycloalkyl contains at least one atom selected from among N, O, and S in the ring;

is bidentate ligand formed with coordinate bond with iridium;

m is 2 or 3.)

[Formula 2]

(In Formula 2 above, $L^1$ to $L^3$ are independent ones from each other selected from the group consisting of hydrogen, deuterium, halogen, cyano, $C_1$-$C_{18}$ straight or branched alkyl, $C_1$-$C_{18}$ straight or branched alkoxy, $C_6$-$C_{18}$ aryl, $C_3$-$C_{18}$ cycloalkyl, $C_4$-$C_{18}$ heteroaryl, or 5 to 6-membered heterocycloalkyl, where, the alkyl or alkoxy is non-substitutable or substituted with halogen; the aryl, cycloalkyl, heteroaryl, or heterocycloalkyl is non-substitutable or substituted with halogen or $C_1$-$C_{18}$ straight or branched alkyl; and the heteroaryl or heterocycloalkyl contains at least one atom selected from among N, O, and S in the ring.).

Preferably, the organometallic compound according to the present invention is a compound represented by Formula 1A below.

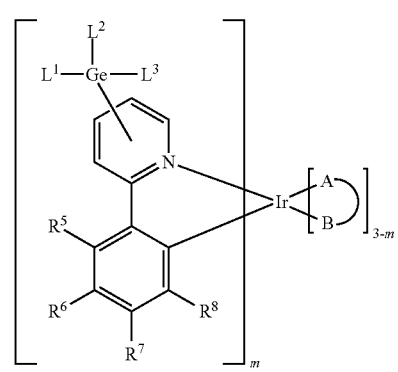

[Formula 1A]

(In Formula 1A above, $L^1$ to $L^3$, $R^5$ to $R^8$,

and m are as defined in Formula 1 and Formula 2 above.)

More preferably, $L^1$ to $L^3$ are independent ones from each other selected from the group consisting of methyl, ethyl, propyl, isopropyl, cyclohexyl, and phenyl.

More preferably, $R^5$ to $R^8$ are independent ones from each other selected from the group hydrogen, methyl, phenyl, methylphenyl, and dimethylphenyl.

More preferably, A and B are independent ones from each other selected from the group consisting of nitrogen (N), oxygen (O), sulfur (S), phosphorus (P), and carbon (C).

More preferably, the bidentate ligand represented as

of Formula 1 is selected from the group consisting of the compounds of the following formulas.

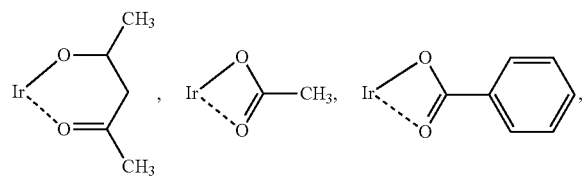

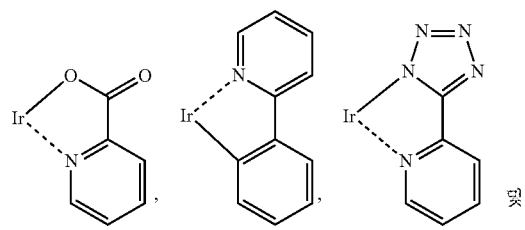

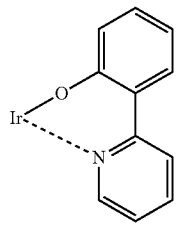

The organometallic compound of Formula 1 may include, as representative example, Ir(PhGe-ppy)$_3$, Ir(MeGe-ppy)$_3$, or Ir(MeGe-ppy)$_2$(acac), but not limited thereto.

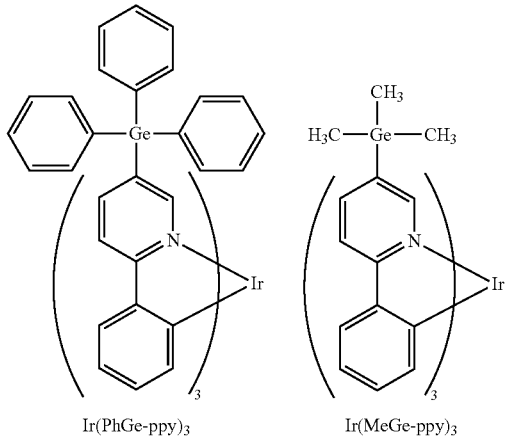

Ir(PhGe-ppy)$_3$      Ir(MeGe-ppy)$_3$

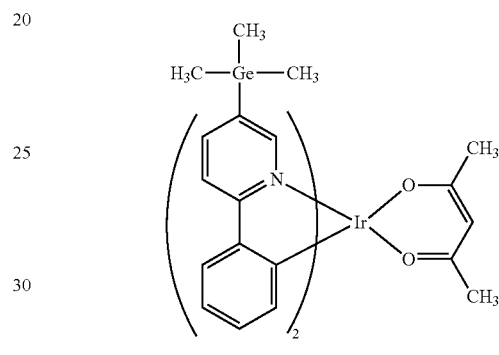

Ir(MeGe-ppy)$_2$(acac)

Further, the present invention provides a method for preparing the novel organometallic compounds.

Preparation Method 1

As shown in Reaction Formula 1 below, the method for preparing novel organometallic compound according to one embodiment includes the following steps of preparing a phenylpyridine compound in which a germanium substituent of Formula 6 is substituted through the reaction between phenylpyridine compound of Formula 4, the compound of Formula 5 containing germanium, and lithium salt (step 1); and preparing an organometallic compound of Formula 1a having coordinate bonding with three main ligand compounds of Formula 6, by mixing the compound of Formula 6 prepared at step 1 with iridium complex in glycerol and refluxing the same (step 2).

[Reaction Formula 1]

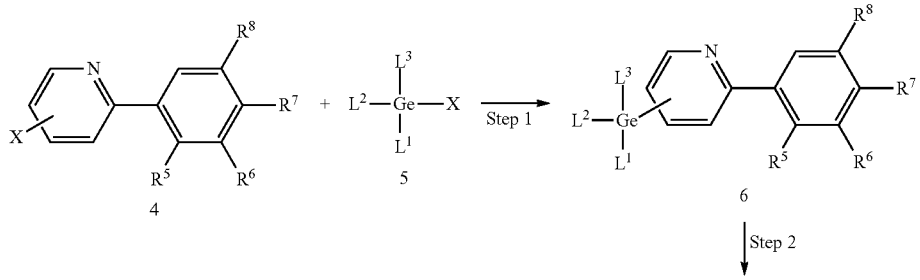

Step 2

-continued

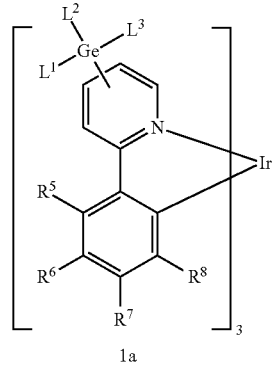

1a (In Reaction Formula 1 above, $L^1$ to $L^3$, $R^5$ to $R^8$,

and m are as defined in Formula 1 and Formula 2; x is halogen atom; and Formula 1a is included in Formula 1.)

Step 1 prepares a phenylpyridine compound in which germanium substituent of Formula 4 is substituted through the reaction of phenylpyridine compound of Formula 2 with the compound containing germanium of Formula 3 and lithium salt.

To be specific, the compound of Formula 2 is added into an organic solvent such as tetrahydrofuran (THF) and diethyl ether, and then the compound containing germanium of Formula 3 and lithium salt are added for reaction, so that the phenylpyridine compound in which the germanium substituent of Formula 4 is substituted, is prepared.

The compounds of Formula 2 and Formula 3 used as a starting material may be commercially available one or prepared using a method generally used in the related industry.

The lithium salt such as n-BuLi, sec-BuLi, or tert-BuLi may be used, and more preferably, n-BuLi may be used.

The temperature for the reaction at step 1 is desirably at a low range of −75~−80° C. After the reaction, a step of purifying the product may be additionally performed using column chromatography.

Next, step 2 prepares an organometallic compound of Formula 1a having coordinate bonding with three main ligand compounds of Formula 6, by mixing the compound of Formula 6 prepared at step 1 with iridium complex compound in glycerol and refluxing the same.

To be specific, the organometallic compound of Formula 1a having coordinate bonding with three main ligand compounds of Formula 6 may be prepared by mixing the compound of Formula 6 with iridium complex compound at a ratio of 2~3:1 mol in glycerol and stirring at reflux temperature for 23~27 hours, followed by cooling off to room temperature and adding acid. Afterwards, extracting with an organic solvent and purifying the product using column chromatography may be additionally performed.

Preparation Method 2

Further, as shown in Reaction Formula 2, a method for preparing novel organometallic compound according to one embodiment includes the following steps of:

preparing phenylpyridine compound in which germanium substituent of Formula 6 is substituted through the reaction of the phenylpyridine compound of Formula 4 with the compound containing germanium of Formula 5 and lithium salt (step A);

preparing diiridium dimer of Formula 7 by mixing the compound of Formula 6 prepared at step A with iridium(III) chloride (IrCl₃) in a solvent for reaction at reflux temperature (step B); and preparing the compound of Formula 1b by adding the diiridium dimer compound of Formula 7 prepared at step B and ancillary ligand compound

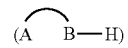

into an organic solvent for coupling reaction (step C).

[Reaction Formula 2]

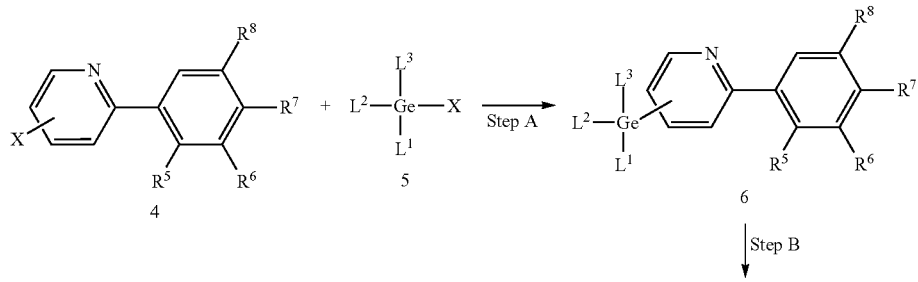

Step B

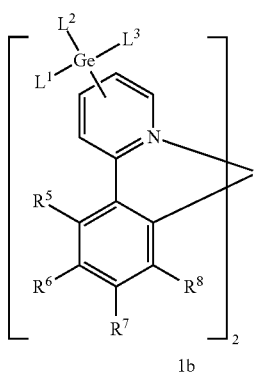

1b

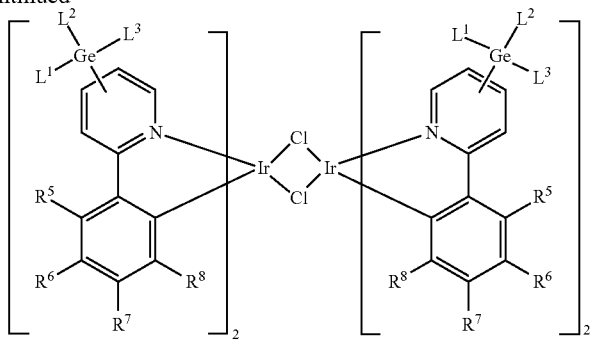

7

(In Reaction Formula 2 above, $L^1$ to $L^3$, $R^5$ to $R^8$,

and m are as defined in Formula 1 and Formula 2. X is halogen atom. Formula 1b is included in Formula 1.)

First, the step A prepares phenylpyridine compound in which the germanium substituent of Formula 6 is substituted, which may be performed in the same manner as step 1 for Formula 1.

Next, the step B prepares diiridium dimer of Formula 7 by mixing the compound of Formula 6 prepared at the step A with iridium(III) chloride ($IrCl_3$) in a solvent for reaction at reflux temperature.

To be specific, iridium(III) chloride ($IrCl_3$) and the compound of Formula 6 as a main ligand are mixed together at a ratio of 1:2~3 mol in a solvent. After reflux, diiridium dimer is separated. The solvent used at this step may desirably be alcohol or alcohol/water mixed solvent, e.g. 2-ethoxyethanol and 2-ethoxyethanol/water mixed solvent.

Next, the step C prepares the compound of Formula 1b by adding the diiridium dimer compound of Formula 7 prepared at the step B and ancillary ligand compound

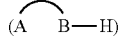

into an organic solvent for coupling reaction.

To be specific, the separated diiridium dimer is mixed with ancillary ligand compound

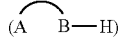

in the organic solvent. After heating, the organometallic compound with the ratio of main ligand:ancillary ligand at 2:1 is prepared as end product. Molar ratio between the main ligand and ancillary ligand of the end product is determined properly, in which, $AgCF_3SO_3$, $Na_2CO_3$, or NaOH may be mixed with the organic solvent—2-ethoxyethanol, 2-methoxyethyl ether, or 1,2-dichloroethane—for reaction.

The organometallic compound of Formula 1 according to one embodiment contains at least one germanium substituent of Formula 2 so that intermolecular interaction of the organometallic compound is inhibited in a solid state and performance of the organic light-emitting diode, particularly light-emitting efficiency, is improved compared to unsubstituted compounds.

In addition to the above, the organometallic compound of Formula 1 according to one embodiment contains at least one germanium substituent of Formula 2 so that the solubility in organic solvent is increased, compared to unsubstituted compounds. Accordingly, the concentration of the compound of Formula 1 in a solution may be increased when forming an organic thin film containing the organometallic compound of Formula 1.

Thus, the organometallic compound of Formula 1 according to one embodiment may be used effectively in the solution process through the introduction of a germanium substituent into a parent iridium organometallic compound, inhibiting intermolecular interaction in a solid state. Further, the organometallic compound may be used effectively as a material for an organic light-emitting diode, since the emission efficiency is improved significantly when used as part of light-emitting layer of the organic light-emitting diode.

The solution process may include, for example, spin coating, inkjet printing, screen printing, or gravure printing. Alternatively, the compound of Formula 1 according to one embodiment may be applicable to such general methods for forming a thin film as vacuum deposition and dip coating.

Further, the present invention provides an organic light-emitting diode containing an organometallic compound of Formula 1 in the light-emitting layer.

The organic light-emitting diode according to one embodiment is a single layer form including an integrated structure of an anode and a cathode, and a light-emitting layer containing the compound of Formula 1 as a light-emitting host material between the two electrodes, or a multilayer form including a charge transfer layer, an anode, a light-emitting layer containing the compound of Formula 1 as a light-emitting material, and a cathode stacked on each other in sequence.

To be specific, the organic light-emitting diode including a first electrode, a second electrode, and one or more organic layers interposed between the first electrode and second electrode, the organic layer may include one or more organometallic compounds of Formula 1.

Generally, the multilayer diode composed of a combination of the light-emitting layer and charge transfer layer may present a more desirable property than the single layer diode composed of one light-emitting layer only. This is because the light-emitting material and the charge transfer material are properly combined, thus reducing energy barrier when the charge is injected from the electrodes and balancing number density between the injected hole and electron due to the charge transfer layer confining the hole or electron injected from the electrodes in the light-emitting layer. Particularly, in the case of phosphorescent light-emitting diode having long emission duration, the multilayer light-emitting diode may be more desirable, since the holes need to be confined in the light-emitting layer for a long time to realize a desirable phosphorescence property and increase the efficiency.

Figure 2:
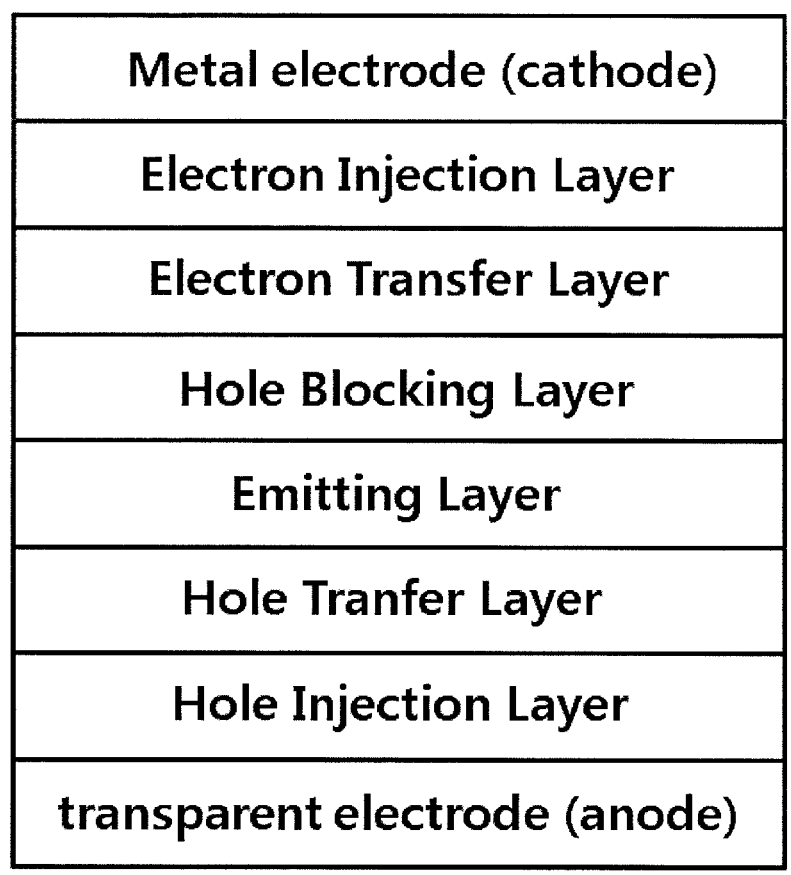
Figure 3:
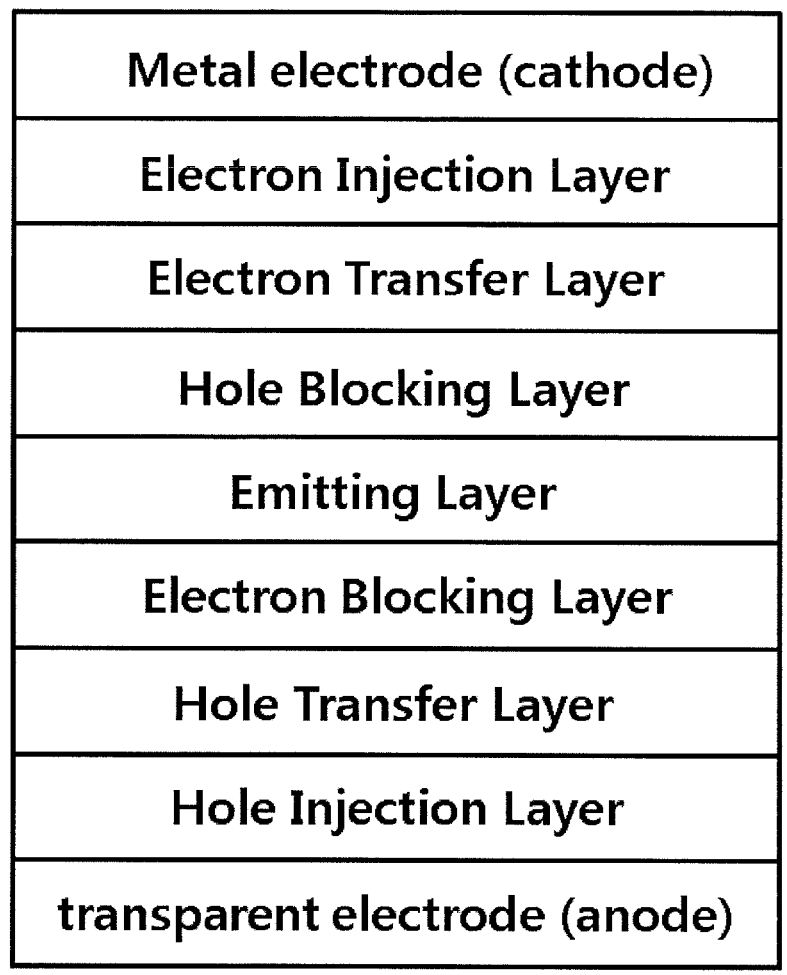

FIGS. 1 to 3 represent schematic cross sections of the organic light-emitting diodes according to one embodiment. As shown in FIG. 1, the organic light-emitting diode is basically composed of a transparent electrode (anode), a hole injection layer, a hole transfer layer, a light-emitting layer, an electron transfer layer, an electron injection layer, and a metal electrode (cathode), which are stacked on each other in regular sequence. As shown in FIG. 2, the hole blocking layer may be included between the light-emitting layer and electron transfer layer to improve the emission efficiency. Further, as shown in FIG. 3, the hole blocking layer and the electron blocking layer may be included additionally between the light-emitting layer and the electron transfer layer, and between the light-emitting layer and the hole transfer layer, respectively.

In the organic light-emitting diode according to one embodiment, the transparent electrode (anode) and the metal electrode (cathode) are formed from general electrode materials. For example, the transparent electrode may be formed from indium tin oxide (ITO) or $SnO_2$, and the metal electrode may be formed from metal such as Li, Mg, Ca, Ag, Al, and In, and alloy of the above metals. The metal electrode may be single-layered or multilayered having e.g. two or more layers.

The light-emitting layer may be single-layered or multi-layered having e.g. two or more layers, for which the compound of Formula 1 may be used as dopant. The light-emitting layer may additionally contain one or more phosphorescent dopants other than the compound of Formula 1. The phosphorescent dopant is the one generally used in the relevant industry, which may be selected from the group consisting of tris(2-phenylpyridinato-N,C2)ruthenium, bis(2-phenylpyridinato-N,C2)palladium, bis(2-phenylpyridinato-N,C2)platinum, tris(2-phenylpyridinato-N,C2)osmium, tris(2-phenylpyridinato-N,C2)rhenium, platinum octaethyl porphyrin, platinum octaphenyl porphyrin, palladium octaethyl porphyrin, palladium octaphenyl porphyrin, iridium (III)bis[(4,6-difluorophenyl)-pyridinato-N,C2']picolinate (Firpic), tris(2-phenylpyridinato-N,C2) iridium (Ir(ppy)$_3$), fac-Ir(ppy)$_3$, bis-(2-phenylpyridinato-N,C2) iridium(acetylacetonate) (Ir(ppy)$_2$(acac)), and 2,3,7,8,12,13,17,18-octaethyl-21H,23H-porphyrin platinum (II) (PtOEP).

The hole transfer layer may contain a general hole transfer material such as 4,4-bis[N-(1-naphthyl)-N-phenyl-amine] biphenyl(α-NPD), N,N-diphenyl-N,N-bis(3-methylphenyl)-1,1-biphenyl-4,4-diamine(TPD), and poly-(N-vinylcarbazole) (PVCz), singly or as a mixture of two or more. Two or more hole transfer layers may be stacked separately.

The hole blocking layer has the lowest unoccupied molecular orbital (LUMO) value between 5.5 and 7.0. The hole blocking layer is composed of materials having a desirable electron transferability, yet a considerably low hole transferability, and for which such materials as bathocuproine (BCP), 3-(4-biphenylyl)-4-phenyl-5-(4-t-butylphenylyl)-1,2,4-triazole (TAZ), and bis(8-hydroxy-2-methylquinolinato)-aluminum biphenoxide (BAlq) are desirable. Further, the electron blocking layer generally contains a material with a large LUMO value, and for which iridium (III)tris(1-phenylpyrazole-N,C2')(Ir(ppz)$_3$) is desirable.

The electron transfer layer (electron transferable light-emitting layer) may be composed of general electron transfer materials, e.g., tris(8-quinolinolato)aluminum (Alq$_3$) or rubrene, independently or with two or more mixed. Two or more electron transfer layers may be stacked separately.

In order to improve the diode properties including emission efficiency and lifespan, a general hole injection layer containing copper phthalocyanine (CuPc) may be inserted between anode and the hole transfer layer, and a general electron injection layer containing LiF may be inserted between cathode and the electron transfer layer.

The anode, cathode, light-emitting layer, transfer layers, injection layers, and blocking layers may be formed using a general deposition method.

Further, the present invention provides a method for forming a thin film for an organic light-emitting diode, which includes the following steps of:

preparing a solution by dissolving the organometallic compound of Formula 1 in an organic solvent (step 1); and forming a thin film on a substrate by dropping the solution prepared at step 1 onto the substrate, and rotating and drying the substrate (step 2).

The organometallic compound of Formula 1 according to one embodiment contains at least one germanium substituent of Formula 2, and thus has an increased solubility in organic solvent compared to unsubstituted compound. Therefore, when forming an organic thin film containing the organometallic compound of Formula 1 in solution, the concentration of the compound of Formula 1 in the solution may be increased.

The organic solvent used may be 1,2-dichloroethane, chlorobenzene, or toluene, but not limited thereto.

Hereinafter, the present invention will be described in greater detail with examples. However, the following examples are intended only to be illustrative, and not to limit the scope of the claims.

Preparation Example 1

Preparation of 3-bromo-6-phenylpyridine 2,5-dibromopyridine (8 g, 33.77 mmol), phenylboronic acid (5.35 g, 43.9 mmol), and tetrakis triphenyl palladium (0.97 g, 0.84 mmol) were dissolved in anhydrous tetrahydrofuran (100 mL). Into this solution, aqueous solution (33.7 mL) of sodium carbonate (9.33 g, 67.54 mmol) was added and reacted at 75° C. for 16 hours. Afterwards, the reactant was concentrated at reduced pressure and extracted with water (100 mL) and dichloromethane (50 mL×3 times) to separate an organic layer. The obtained organic layer was dried with anhydrous magnesium sulfate and concentrated at reduced pressure. The end product was purified through silica-gel column chromatography using dichloromethane/hexane=1/1 as a developer so that a white solid target compound was obtained (5.18 g, Yield 65%).

$^1$H-NMR (300 MHz, CDCl$_3$) δ 7.65 (m, 3H), 7.80 (d, 1H), 7.95 (d, 1H), 8.05 (d, 2H), 8.95 (s, 1H).

Example 1

Preparation of Ir(PhGe-ppy)$_3$

Step 1: Preparation of 3-(triphenylgermyl)-6-phenylpyridine

The 3-bromo-6-phenylpyridine (0.86 g, 3.67 mmol) prepared in accordance with Preparation Example 1 was dissolved in anhydrous tetrahydrofuran (20 mL) and stirred at −78° C. Into this solution, n-butyllithium (1.76 mL, 4.41 mmol, 2.5M hexane solution) was added drop-by-drop for approximately 20 minutes. After stirring additionally for 1 hour, triphenylgermanium chloride (1.5 gm 4.41 mmol) was added and reacted overnight at room temperature. Afterwards, water (100 mL) was poured to separate water layer and organic layer. The organic layer was additionally extracted with diethyl ether (80 mL×2 times), dried with anhydrous magnesium sulfate, and concentrated at reduced pressure. The end product was purified through silica-gel column chromatography using diethyl ether/hexane=1/10 as a developer so that a white solid target compound was obtained (0.52 g, Yield 31%).

$^1$H-NMR (300 MHz, CDCl$_3$) δ 7.48 (m, 18H), 7.75 (d, 1H), 7.89 (d, 1H), 8.03 (d, 2H), 8.81 (s, 1H).

Step 2 Preparation of Ir(PhGe-ppy)$_3$

The 3-(triphenylgermyl)-6-phenylpyridine (1 g, 2.18 mmol) prepared at Step 1 and iridium (III) acetylacetonate (0.305 g, 0.623 mmol) were dissolved in glycerol (30 mL) and stirred at 230° C. for 25 hours. After cooling to room temperature, 1N hydrochloric acid was added and precipitate was filtered. The filtrate was extracted with water (50 mL) and dichloromethane (40 mL×3 times) to separate organic layer. The obtained organic layer was dried with anhydrous magnesium sulfate and concentrated at reduced pressure. The end product was purified through silica-gel column chromatography using dichloromethane/hexane=1/1 as a developer so that a yellow solid target compound was obtained (0.238 g, Yield 24%).

$^1$H-NMR (300 MHz, Acetone d$_6$) δ 6.7 (t, 1H), 6.85 (t, 2H), 7.19 (m, 12H), 7.35 (m, 3H), 7.54 (d, 1H), 7.62 (s, 1H), 7.76 (d, 1H), 7.85 (d, 1H).

Example 2

Preparation of Ir(MeGe-ppy)$_3$

Step 1: Synthesis of 3-(trimethylgermyl)-6-phenylpyridine

The 3-bromo-6-phenylpyridine (3.48 g, 14.88 mmol) prepared in accordance with Preparation Example 1 was dissolved in anhydrous tetrahydrofuran (50 mL) and stirred at −78° C. Into this solution, n-butyllithium (7.14 mL, 17.86 mmol, 2.5M hexane solution) was added drop-by-drop for approximately 20 minutes. After stirring additionally for 1 hour, chlorotrimethylgermanium (2.19 g, 17.86 mmol) was added and reacted overnight at room temperature. Afterwards, water (100 mL) was poured to separate water layer and organic layer. The organic layer was additionally extracted with diethyl ether (80 mL×2 times), dried with anhydrous magnesium sulfate, and concentrated at reduced pressure. The end product was purified through silica-gel column chromatography using diethyl ether/hexane=1/10 as a developer so that a yellow liquid target compound was obtained (1.24 g, Yield 42%).

$^1$H-NMR (300 MHz, CDCl$_3$) δ 0.49 (s, 9H), 7.48 (m, 3H), 7.71 (m, 1H), 7.81 (m, 1H), 8.01 (m, 2H), 8.74 (m, 1H).

Step 2: Preparation of Ir(MeGe-ppy)$_3$

The 3-(trimethylgermyl)-6-phenylpyridine (2.49 g, 9.16 mmol) prepared at Step 1 and iridium (III) acetylacetonate (1.28 g, 2.61 mmol) were dissolved in glycerol (60 mL) and stirred at 230° C. for 25 hours. After cooling to room temperature, 1N hydrochloric acid was added and precipitate was filtered. The filtrate was extracted with water (50 mL) and dichloromethane (40 mL×3 times) to separate organic layer. The obtained organic layer was dried with anhydrous magnesium sulfate and concentrated at reduced pressure. The end product was purified through silica-gel column chromatography using dichloromethane/hexane=1/1 as a developer so that a yellow solid target compound was obtained (0.47 g, Yield 18%).

$^1$H-NMR (300 MHz, Acetone d$_6$) δ 0.22 (s, 9H), 6.80 (m, 2H), 6.98 (d, 1H), 7.49 (s, 1H), 7.73 (d, 1H), 7.88 (d, 1H), 8.04 (d, 1H).

Example 3

Preparation of Ir(MeGe-ppy)$_2$(acac)

Step A: Preparation of 3-(trimethylgermyl)-6-phenylpyridine

Step A was performed in the same manner as Step 1 of Example 2.

Steps B and C: Preparation of Ir(MeGe-ppy)$_2$(acac)

The 3-(trimethylgermyl)-6-phenylpyridine (1.61 g, 5.91 mmol) prepared at Step A and iridium (III) acetylacetonate (0.53 g, 1.77 mmol) were dissolved in 2-ethoxyethanol (30 mL) and water (10 mL), and stirred at 125° C. for 12 hours. After cooling to room temperature, excessive water was poured and precipitate was filtered so that cyclometallated Ir(III)μ-chloro bridged dimer was obtained (0.60 g, Yield 44%)(Step B).

Without additional purification, the dimer compound obtained from Step B was dissolved with acetylacetone (0.10 g, 1.00 mmol) and sodium carbonate (0.41 g, 3.9 mmol) in 2-ethoxyethanol (10 mL), and refluxed and heated at 170° C. for 12 hours. A solid created while cooling to room temperature after the reaction was concluded was filtered and then cleaned with water. The end product was purified through silica-gel column chromatography using dichloromethane as a developer so that a yellow solid target compound was obtained (0.19 g, Yield 30%).

$^1$H-NMR (300 MHz, CDCl$_3$) δ 0.49 (s, 18H), 1.77 (s, 6H), 2.05 (s, 6H), 5.19 (s, 1H), 7.45 (m, 6H), 7.67-7.85 (m, 4H), 7.99 (m, 4H).

Example 4

Fabrication and Property Evaluation of Organic Light-Emitting Diode Using Ir(PhGe-Ppy)$_3$ After ultrasonically cleaning a patterned ITO substrate with acetone and isopropanol for 10 minutes each, the substrate was dried under a stream of nitrogen. Afterwards, 20 minutes of dry cleaning was performed additionally in a UV/O$_3$ cleaning apparatus. On the cleaned ITO substrate, PEDOT:PSS (CLEVIOS™ P VP AI 4083) was spin-coated at 4200 rpm for 30 seconds. After drying the substrate in a 120° C. vacuum oven for 1 hour, a 40 nm-thin film was formed. PVK (Sigma-Aldrich Catalog No. 368350), TPD (Sigma-Aldrich Catalog No. 443263), PBD (Sigma-Aldrich Catalog No. B8378), and Ir(PhGe-ppy)$_3$ synthesized in accordance with Example 1 were mixed together at a ratio of 50:10:31:9 (mass ratio), followed by adding 1,2-dichloroethane so that a total solid concentration became 1.3 m % (mass percentage), and thereby an organic light-emitting layer composition was prepared. The solution of the organic light-emitting layer composition spin-coated on the PEDOT:

PSS-coated ITO substrate at 1500 rpm for 30 seconds. After drying the substrate on a 55° C. hotplate, a 80 nm-thin film was formed. The spin coating and drying of the organic light-emitting composition solution was performed in a glove box under nitrogen atmosphere. The ITO substrate coated with PEDOT:PSS and the organic light-emitting composition was moved into a vacuum deposition chamber to deposit cesium fluoride and aluminum to 1 nm and 120 nm, respectively, under 10 torr vacuum. After sealing up the finished organic light-emitting diode in the glove box with glass cover and epoxy sealant, the properties of the organic light-emitting diode were evaluated using PR-650 Spectrascan calorimeter and Keithley 2400 Sourcemeter.

Example 5

Fabrication and Property Evaluation of Organic Light-Emitting Diode Using Ir(MeGe-ppy)$_3$ The organic light-emitting diode was prepared and the properties thereof were evaluated in the same manner as presented in Example 4, except for using Ir(MeGe-ppy)$_3$ synthesized in accordance with Example 2 instead of Ir(PhGe-ppy)$_3$ as a constituent of the organic light-emitting composition solution.

Comparative Example 1

Fabrication and Property Evaluation of Organic Light-Emitting Diode Using Ir(Ppy)$_3$ The organic light-emitting diode was prepared and the properties thereof were evaluated in the same manner as presented in Example 4, except for using Ir(ppy)$_3$ (Lumtec Catalog No. LT-E504) used as a conventional organic light emitter, instead of Ir(PhGe-ppy)$_3$ as a constituent of the organic light-emitting composition solution.

The emission spectra of the organic light-emitting diodes presented in Example 4, Example 5, and Comparative Example 1 were measured. The results of the measurement are provided in FIG. 4. The graph showing the current density and emission efficiency is provided in FIG. 5. The graph showing voltage-luminance/voltage-current is provided in FIG. 6. Based on the above, the properties of the organic light-emitting diodes are summarized in Table 1 below.

TABLE 1

|  | Maximum Emission Wavelength (nm) | CIE Color Coordinates (x, y) | Maximum Current Efficiency (cd/A) |
|---|---|---|---|
| Ex. 4 | 524 | (0.35, 0.61) | 20.9 |
| Ex. 5 | 520 | (0.33, 0.62) | 23.0 |
| Comp. Ex. 1 | 512 | (0.31, 0.61) | 17.0 |

Figure 4:
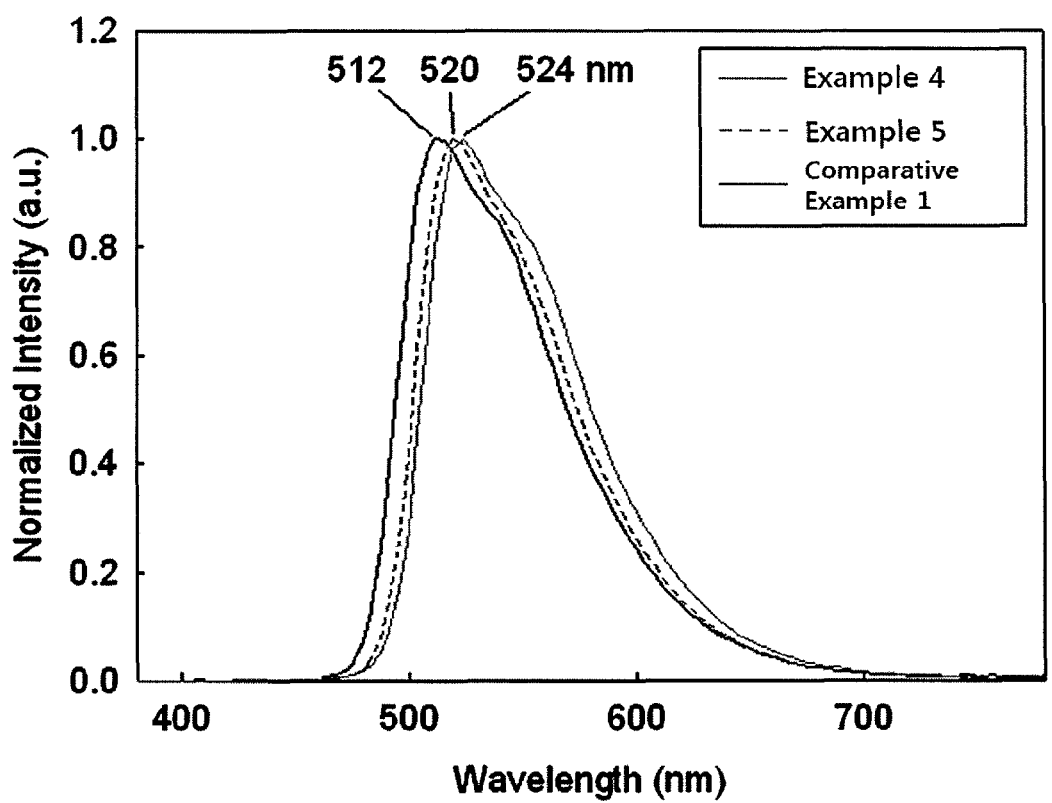
FIG. 4 shows the emission spectra of the organic light-emitting diodes prepared in accordance with Example 4, Example 5, and Comparative Example 1 of the present invention.
Figure 5:
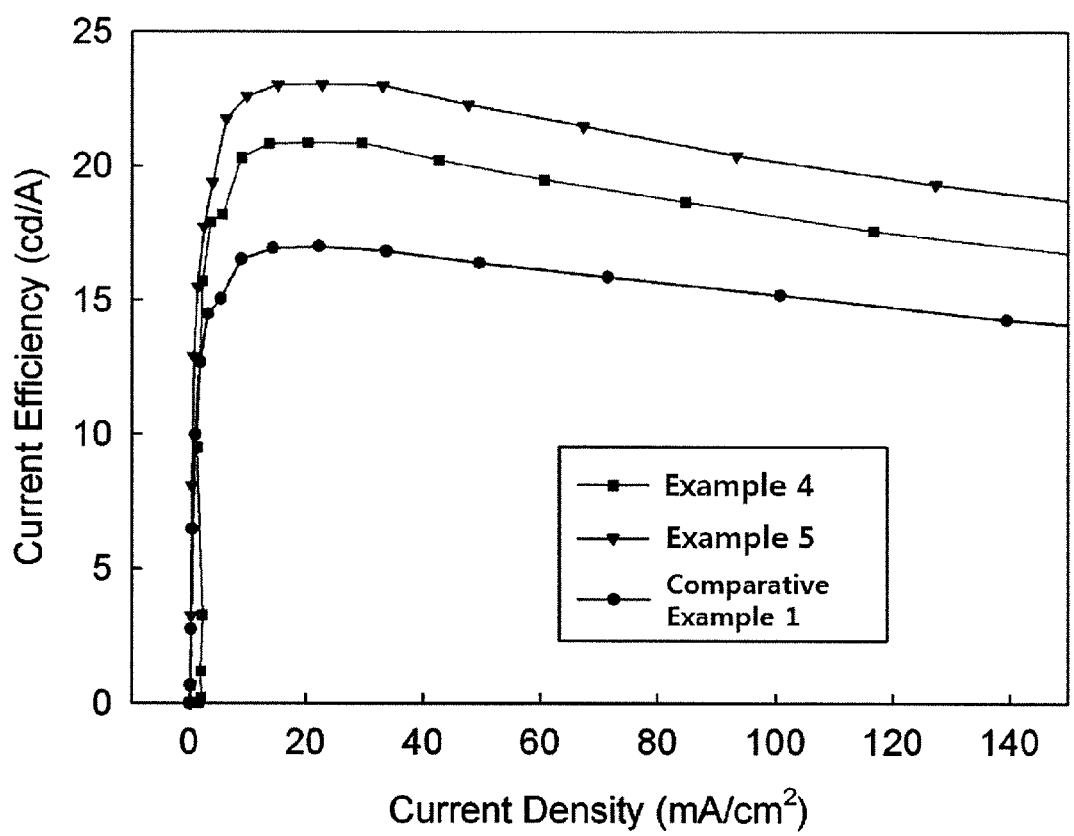
FIG. 5 is a current density-emission efficiency graph of the organic light-emitting diodes prepared in accordance with Example 4, Example 5, and Comparative Example 1 of the present invention.
Figure 6:
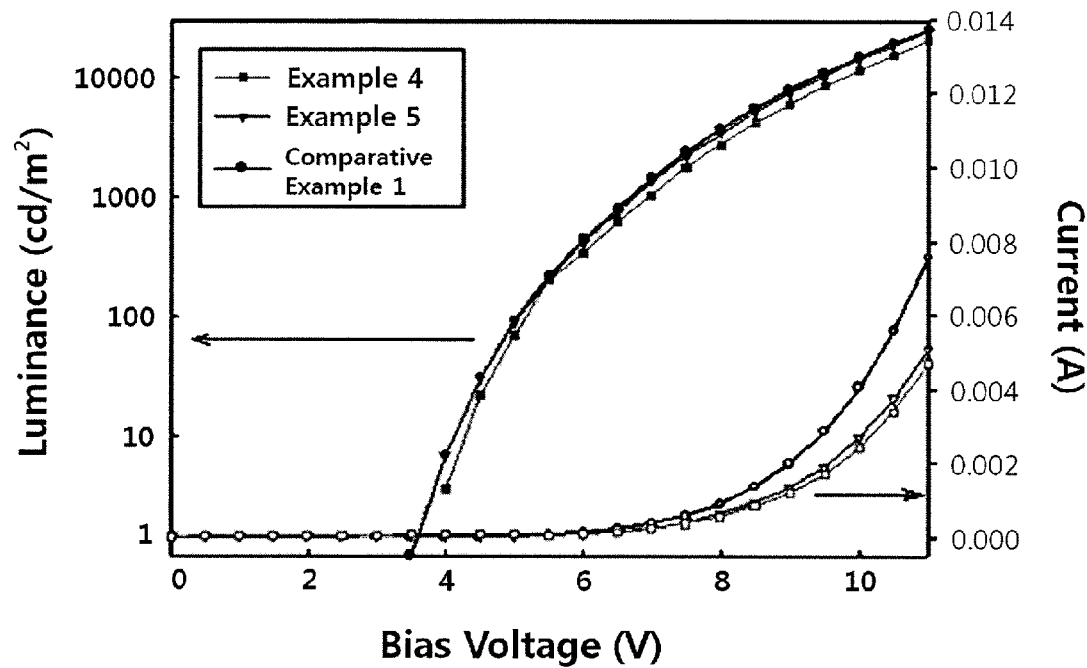
FIG. 6 is a voltage-luminance/voltage-current graph of the organic light-emitting diodes prepared in accordance with Example 4, Example 5, and Comparative Example 1 of the present invention.

As shown in FIGS. 4 to 6 and Table 1, it was confirmed that the germanium-substituted Ir(PhGe-ppy)$_3$ and Ir(MeGe-ppy)$_3$ of the present invention demonstrated a more desirable performance as a light-emitting material in the organic light-emitting layer of the organic light-emitting diode, compared to Ir(ppy)$_3$ used as a comparative material. Further, it was confirmed that the emission efficiency of the organic light-emitting diode can be improved by introducing germanium substituent into the organic light-emitting material.

Therefore, the compound according to one embodiment may improve the emission efficiency significantly if used as part of the light-emitting layer of an organic light-emitting diode and thus may be used effectively as a material for the organic light-emitting diode.

Example 6

Fabrication and Property Evaluation of Multilayer Organic Light-Emitting Diode Using Ir(MeGe-ppy)$_3$ In the same manner as presented in Example 4, the ITO substrate was cleaned and PEDOT:PSS film was formed thereupon. Afterwards, poly(triphenylamine) solution (0.12 m %, solvent: chlorobenzene) was spin-coated at 1500 rpm for 30 seconds, followed by drying on a 100° C. hotplate so that a 10 nm-thin film of the hole transfer layer was formed. PVK (Sigma-Aldrich Catalog No. 368350), TPD (Sigma-Aldrich Catalog No. 443263), PBD (Sigma-Aldrich Catalog No. B8378), and Ir(MeGe-ppy)$_3$ synthesized in accordance with Example 2 were mixed together at a ratio of 73:10:10:7 (mass ratio), followed by adding 1,2-dichloroethane so that a total solid concentration became 0.64 m % (mass percentage) and thereby an organic light-emitting layer composition was prepared. The solution of the organic light-emitting layer composition spin-coated on the PEDOT:PSS and poly (triphenylamine) coated ITO substrate at 1800 rpm for 30 seconds. After drying the substrate on a 55° C. hotplate, a 50 nm-thin film of the organic light-emitting layer was formed. The spin coating and drying of the hole transfer layer composition solution and the organic light-emitting composition solution were performed in a glove box under nitrogen atmosphere. The ITO substrate coated with PEDOT:PSS, the hole transfer layer composition, and the organic light-emitting composition was moved into a vacuum deposition chamber to deposit TPBi (1,3,5-Tri(1-phenyl-1H-benzo[d] imidazol-2-yl)phenyl, Lumtec Catalog No. LT-E302) to 57 nm under $10^{-7}$ torr vacuum so that an electron transfer layer was formed. Again, cesium fluoride and aluminum were deposited thereupon at 1 nm and 120 nm, respectively. After sealing up the finished organic light-emitting diode in the glove box with glass cover and epoxy sealant, the properties of the organic light-emitting diode were evaluated using PR-650 Spectrascan calorimeter and Keithley 2400 Sourcemeter.

Figure 7:
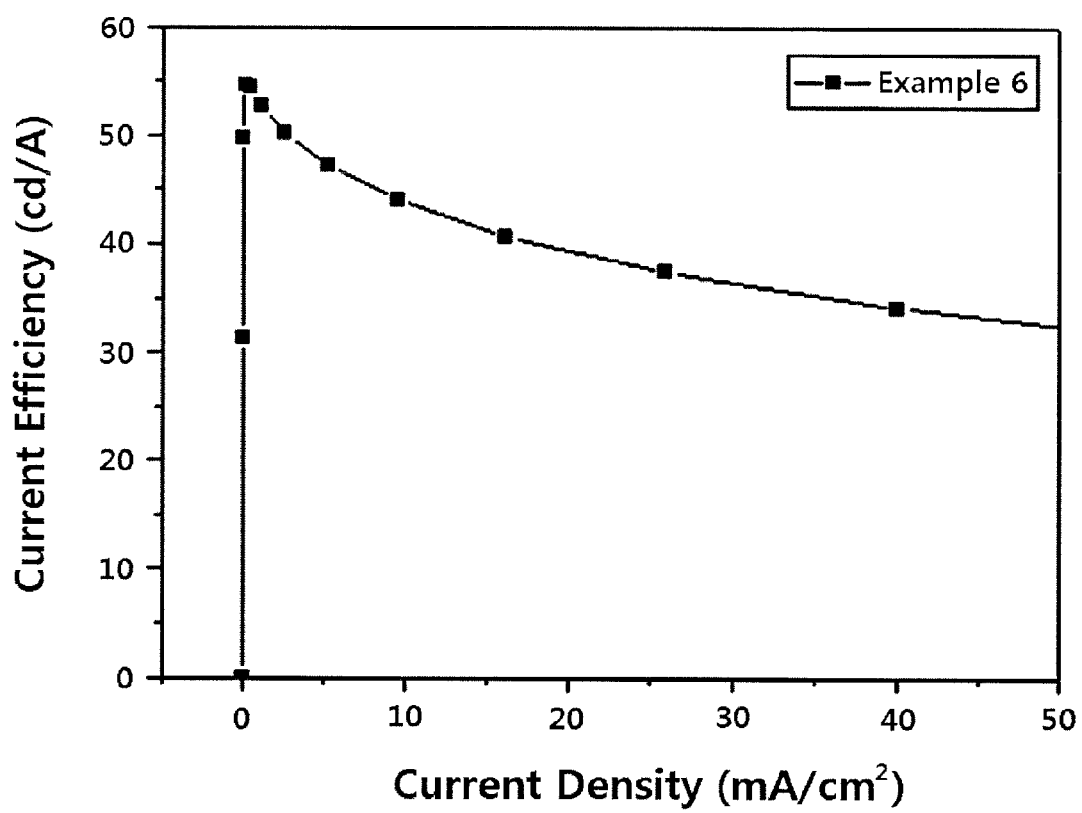
FIG. 7 is a current density-emission efficiency graph of the multilayer organic light-emitting diode prepared in accordance with Example 6 of the present invention.
Figure 8:
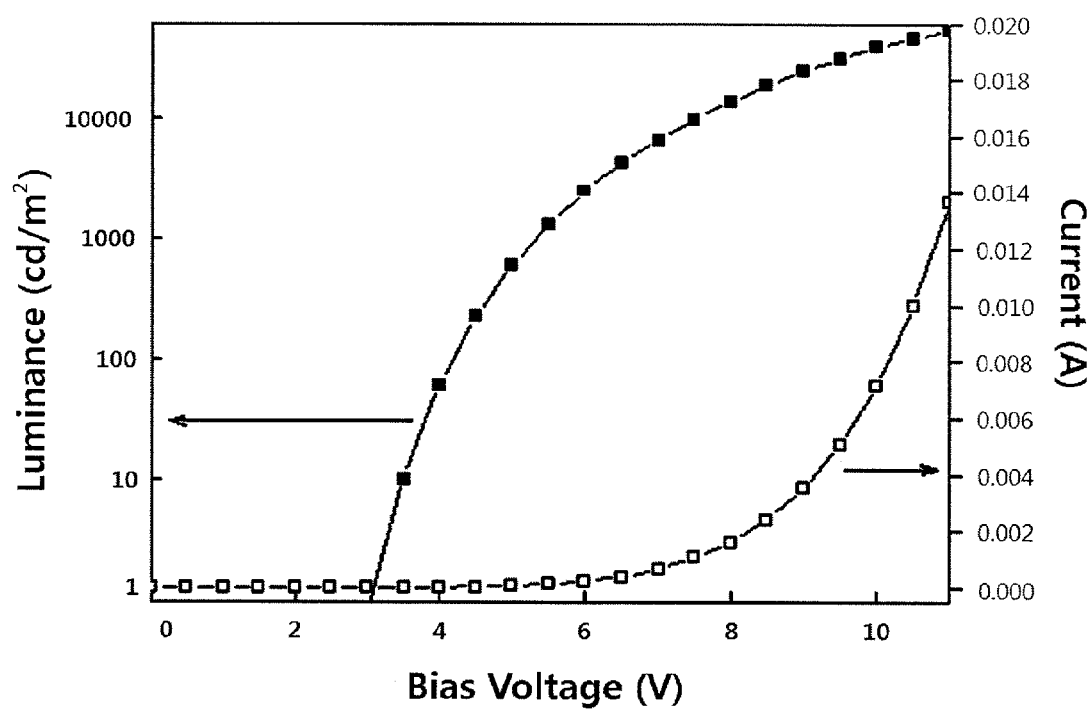
FIG. 8 is a voltage-luminance/voltage-current graph of the multilayer organic light-emitting diode prepared in accordance with Example 6 of the present invention.

The graph representing the current density-emission efficiency of the organic light-emitting diode of Example 6 is provided in FIG. 7, and the graph of the voltage-luminance/voltage-current in FIG. 8.

Result

As shown in FIG. 7 and FIG. 8, it was confirmed that the multilayer organic light-emitting diode prepared using germanium-substituted Ir(MeGe-ppy)$_3$ according to one embodiment demonstrated desirable properties.

Therefore, the germanium-substituted Ir(MeGe-ppy)$_3$ according to one embodiment may be used effectively for an organic light-emitting diode.

The present invention has been hitherto described with desirable examples. Those skilled in the relevant fields of expertise to which the present invention pertains may understand that the present invention may be realized in a modified form within a range of intrinsic properties of the present invention. Hence, the examples presented herein shall be considered from an explanatory perspective, not from a limited perspective. The scope of the present invention is disclosed in the claims hereinafter, not in the foregoing description. Therefore, all the discrepancies within the same scope shall be considered included in the present invention.

What is claimed is:

1. An organometallic compound represented by Formula 1 below

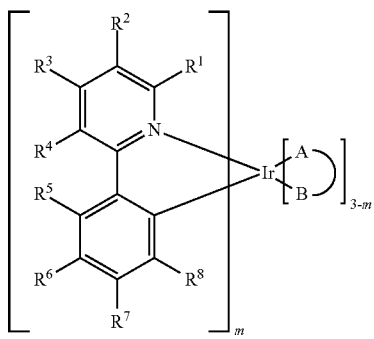

[Formula 1]

(in Formula 1 above,
at least one among $R^1$ to $R^4$ is a substituent represented by Formula 2 below;
if there is no substituent of Formula 2 among $R^1$ to $R^4$, $R^1$ to $R^4$ are independent ones from each other selected from the group consisting of hydrogen, deuterium, halogen, cyano, $C_1$-$C_{18}$ straight or branched alkyl, $C_1$-$C_{18}$ straight or branched alkoxy, $C_6$-$C_{18}$ aryl, $C_3$-$C_{18}$ cycloalkyl, $C_4$-$C_{18}$ heteroaryl, and 5 to 6-membered heterocycloalkyl, where, the alkyl or alkoxy is non-substitutable or substituted with halogen; the aryl, cycloalkyl, heteroaryl, or heterocycloalkyl is non-substitutable or substituted with halogen or $C_1$-$C_{18}$ straight or branched alkyl; and the heteroaryl or heterocycloalkyl comprises at least one atom selected from among N, O, and S in the ring; and,
$R^5$ to $R^8$ are independent ones from each other selected from the group consisting of hydrogen, deuterium, halogen, cyano, $C_1$-$C_{18}$ straight or branched alkyl, $C_1$-$C_{18}$ straight or branched alkoxy, $C_6$-$C_{18}$ aryl, $C_3$-$C_{18}$ cycloalkyl, $C_4$-$C_{18}$ heteroaryl, and 5 to 6-membered heterocycloalkyl, where, the alkyl or alkoxy is non-substitutable or substituted with halogen; the aryl, cycloalkyl, heteroaryl, or heterocycloalkyl is non-substitutable or substituted with halogen or $C_1$-$C_{18}$ straight or branched alkyl; and the heteroaryl or heterocycloalkyl comprises at least one atom selected from among N, O, and S in the ring; and,

is a bidentate ligand formed with coordinate bond with iridium;
m is 2 or 3),

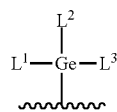

[Formula 2]

(in Formula 2 above,
$L^1$ to $L^3$ are independent ones from each other selected from the group consisting of hydrogen, deuterium, halogen, cyano, $C_1$-$C_{18}$ straight or branched alkyl, $C_1$-$C_{18}$ straight or branched alkoxy, $C_6$-$C_{18}$ aryl, $C_3$-$C_{18}$ cycloalkyl, $C_4$-$C_{18}$ heteroaryl, and 5 to 6-membered heterocycloalkyl, where, the alkyl or alkoxy is non-substitutable or substituted with halogen; the aryl, cycloalkyl, heteroaryl, or heterocycloalkyl is non-substitutable or substituted with halogen or $C_1$-$C_{18}$ straight or branched alkyl; and the heteroaryl or heterocycloalkyl comprises at least one atom selected from among N, O, and S in the ring).

2. An organometallic compound represented by Formula 1A below:

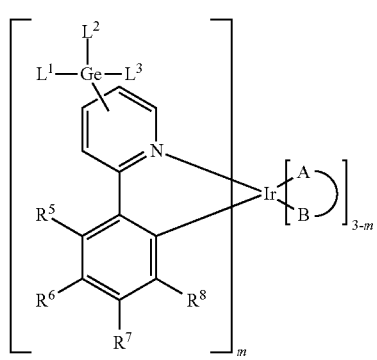

[Formula 1A]

(in the Formula 1A above, $L^1$ to $L^3$, $R^5$ to $R^8$,

and m are as defined in Formula 1 and Formula 2 of claim 1).

3. The organometallic compound according to claim 2, wherein the $L^1$ to $L^3$ are independent ones from each other selected from the group consisting of methyl, ethyl, propyl, isopropyl, cyclohexyl, and phenyl.

4. The organometallic compound according to claim 1, wherein the $R^5$ to $R^8$ are independent ones from each other selected from the group consisting of hydrogen, methyl, phenyl, methylphenyl, and dimethylphenyl.

5. The organometallic compound according to claim 1, wherein the A and B are independent ones from each other selected from among nitrogen (N), oxygen (O), sulfur (S), phosphorus (P), and carbon (C).

6. The organometallic compound according to claim 1, wherein a partial structure, of the organometallic compound represented as

is selected from among compounds of the following formulas:

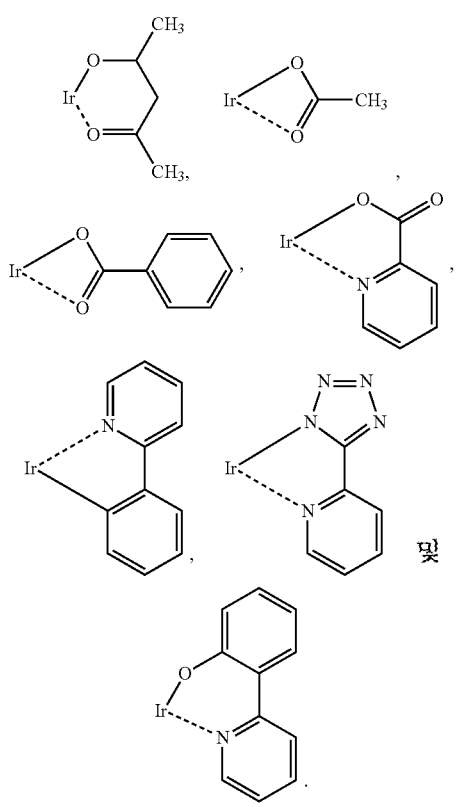

7. The organometallic compound according to claim 1, wherein the organometallic compound is selected from among compounds of the following formulas:

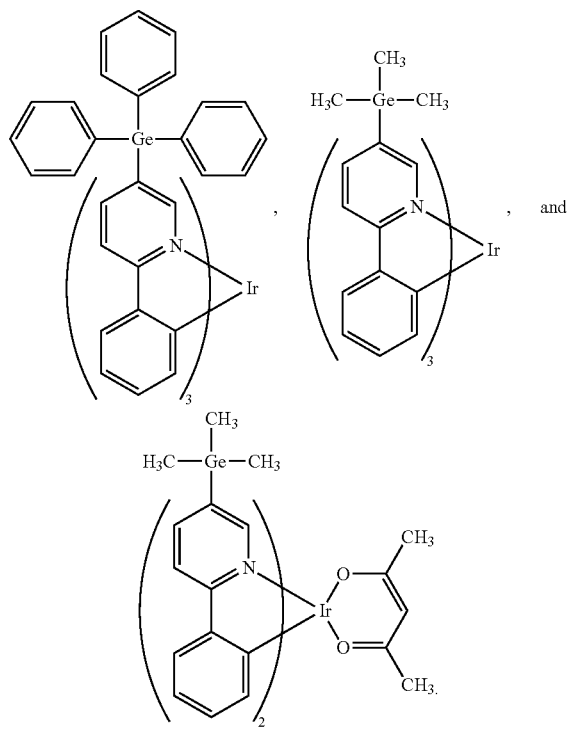

8. An organic light-emitting diode comprising the organometallic compound of claim 1.

9. The organic light-emitting diode according to claim 8, wherein the organometallic compound is used as a dopant of a light-emitting layer.

10. The organic light-emitting diode comprising a first electrode; a second electrode; and one or more organic layers interposed between the first electrode and the second electrode, wherein the organic layer comprises one or more organometallic compounds according to claim 1.

11. A method for forming a thin film for an organic light-emitting diode, the method comprising the following steps of:
   preparing a solution by dissolving the organometallic compound of claim 1 in an organic solvent (step 1); and
   forming a thin film on a substrate by dropping the solution of step 1 onto the substrate and rotating and drying the substrate (step 2).

12. The organometallic compound according to claim 2, wherein the $R^5$ to $R^8$ are independent ones from each other selected from the group consisting of hydrogen, methyl, phenyl, methylphenyl, and dimethylphenyl.

13. The organometallic compound according to claim 2, wherein the A and B are independent ones from each other selected from among nitrogen (N), oxygen (O), sulfur (S), phosphorus (P), and carbon (C).

14. The organometallic compound according to claim 2, wherein a partial structure of the organometallic compound represented as

is selected from among compounds of the following formulas:

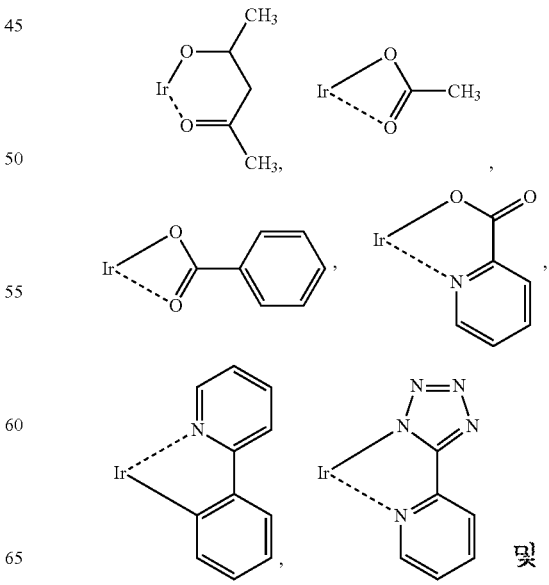

-continued

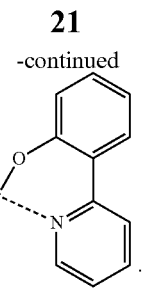

15. The organometallic compound according to claim 2, wherein the organometallic compound is selected from among compounds of the following formulas:

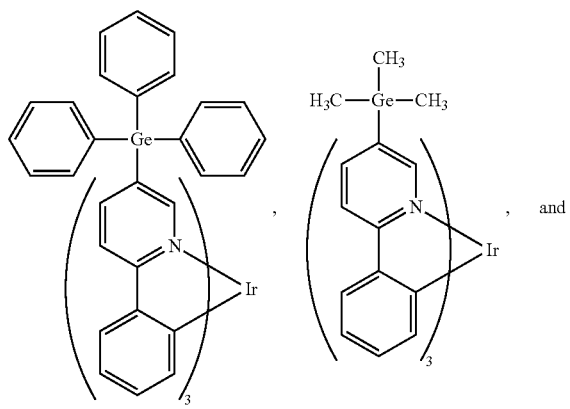

-continued

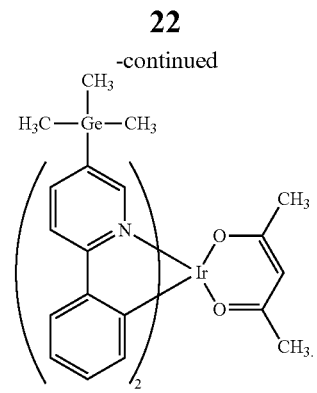

16. An organic light-emitting diode comprising the organometallic compound of claim 2.

17. The organic light-emitting diode comprising a first electrode; a second electrode; and one or more organic layers interposed between the more organometallic compounds according to claim 2.

18. A method for forming a thin film for an organic light-emitting diode, the method comprising the following steps of:

preparing a solution by dissolving the organometallic compound of claim 2 in an organic solvent (step 1); and forming a thin film on a substrate by dropping the solution of step 1 onto the substrate and rotating and drying the substrate (step 2).

* * * * *